United States Patent [19]

Higginbotham et al.

[11] Patent Number: 4,521,115
[45] Date of Patent: Jun. 4, 1985

[54] PULSE CODED OPTICAL ATTENUATION METER

[75] Inventors: John W. Higginbotham, St. Charles County, Mo.; Dennis C. Dowden, Orange County, Fla.

[73] Assignee: McDonnell Douglas Corporation, St. Louis County, Mo.

[21] Appl. No.: 380,705

[22] Filed: May 21, 1982
(Under 37 CFR 1.47)

[51] Int. Cl.$^3$ ............................................ G01N 21/00
[52] U.S. Cl. .................................. 356/432; 356/73.1; 250/214 L
[58] Field of Search ...................... 356/73.1, 432, 433, 356/434, 435, 440, 441, 442, 223; 250/214 L

[56] References Cited

U.S. PATENT DOCUMENTS

| | | | |
|---|---|---|---|
| 3,528,749 | 9/1970 | Bowker | 356/432 |
| 3,746,864 | 7/1973 | Tick et al. | 250/205 |
| 3,755,679 | 8/1973 | Otsuka | 250/205 |
| 3,765,778 | 10/1973 | Bey et al. | 356/434 |
| 3,901,600 | 8/1975 | Johnson et al. | 356/434 |
| 4,124,301 | 11/1978 | Pocock | 356/434 |
| 4,234,253 | 11/1980 | Higginbotham et al. | 356/73.1 |

Primary Examiner—R. A. Rosenberger
Attorney, Agent, or Firm—Polster, Polster and Lucchesi

[57] ABSTRACT

An attenuation measuring system includes a transmitter for generating and transmitting a signal from a first position to a second position, and a receiver adapted to receive the signal at the second position. One of the transmitter and the receiver includes a simple log converter circuit which permits the conversion of an analog signal to a digital signal, so that a time uniform train of pulses is developed, the pulses decreasing in amplitude by equal decibel values. The receiver includes a counter which is counted down from a preset value. The count of the counter is a direct measurement of the loss through a coupling medium between the transmitter and the receiver. The analog-to-digital conversion can be accomplished in either the transmitter or the receiver. When embodied in the receiver, the attenuation meter also can function as an optical power meter.

13 Claims, 8 Drawing Figures

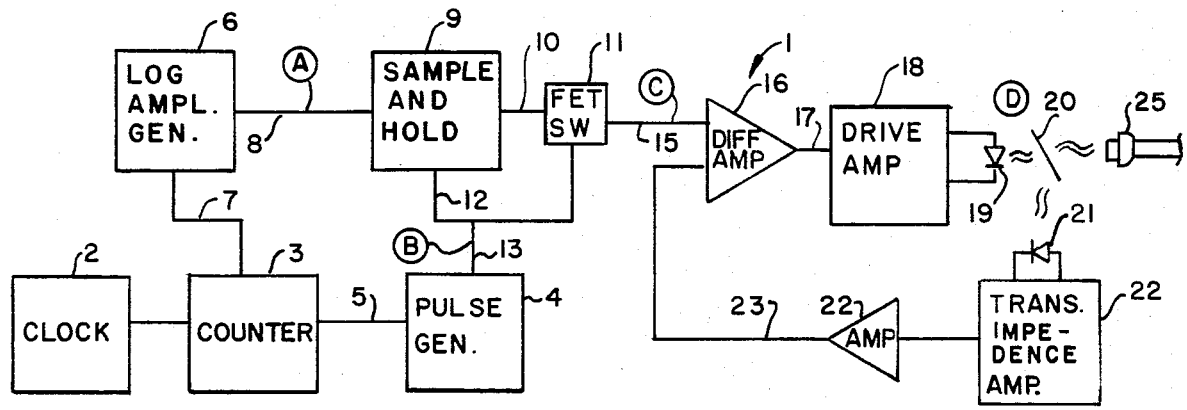
FIG. 1.
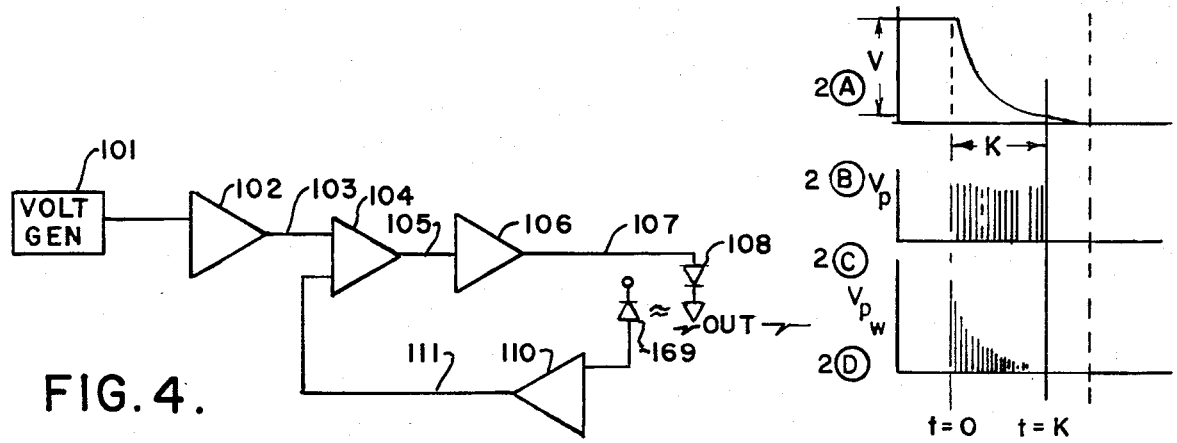
FIG. 4.
FIG. 2.
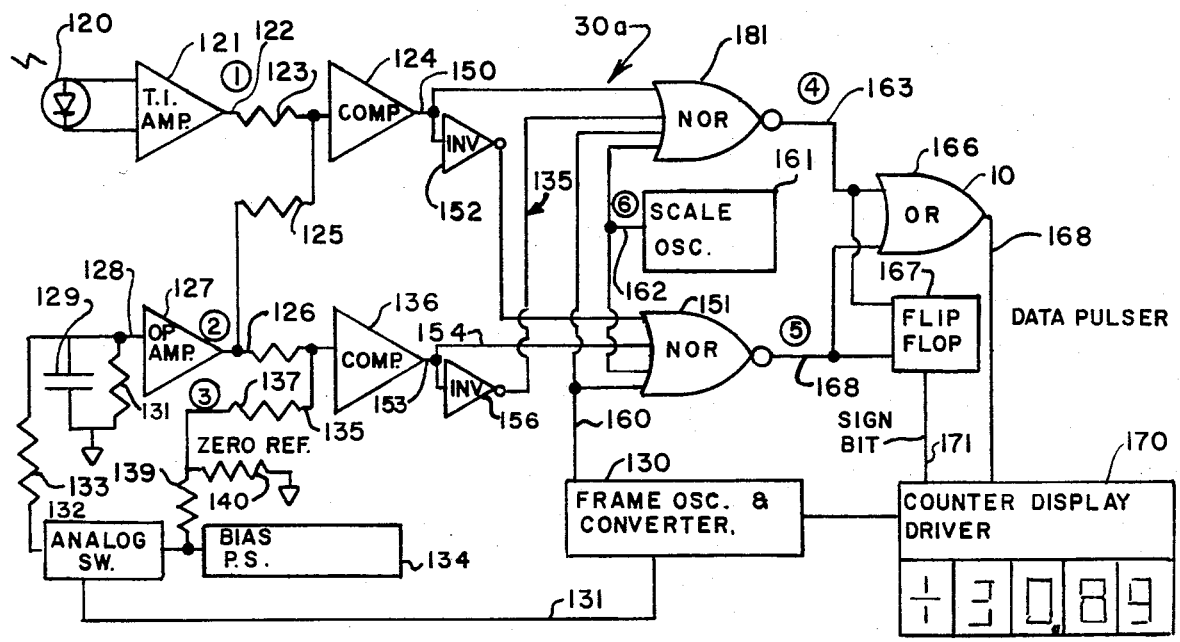
FIG. 5.

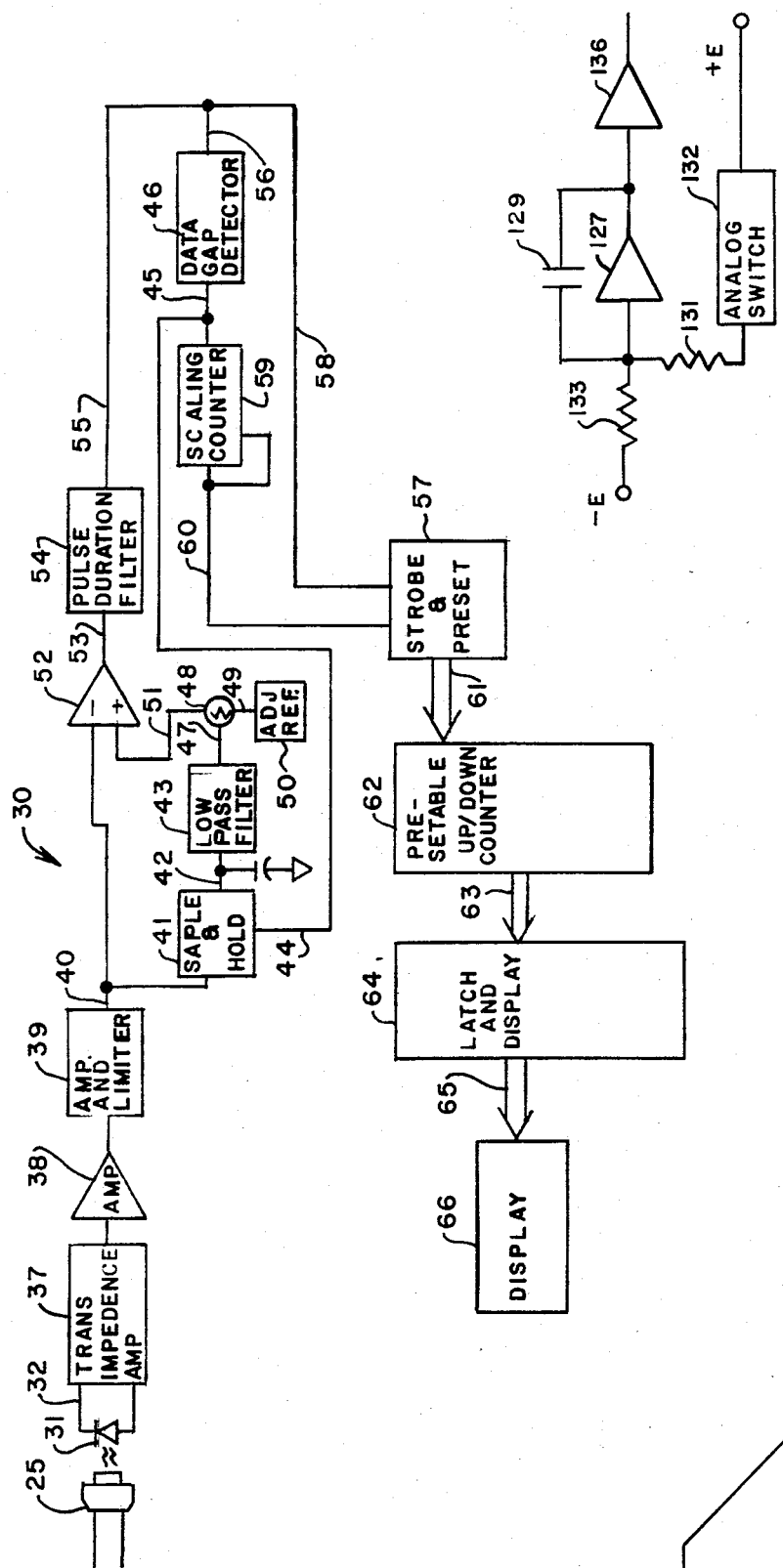
FIG. 3.
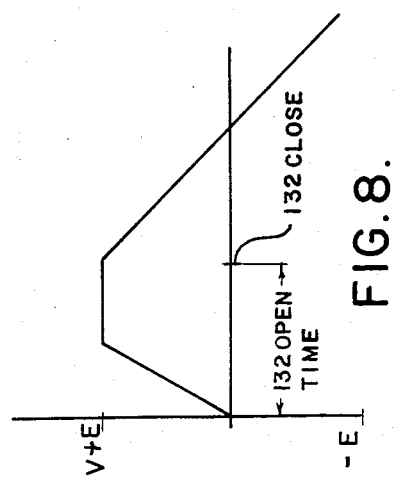
FIG. 7.
FIG. 8.

PULSE CODED OPTICAL ATTENUATION METER

BACKGROUND OF THE INVENTION

This invention relates to a system for testing the attenuation of an electromagnetic wave transmitting medium, and in particular, to a device for testing the attenuation of fiber optic cables. While the invention is described with particular reference to its use with fiber optic cables in aircraft systems, those skilled in the art will recognize the wider applicability of the inventive principles disclosed hereinafter.

Fiber optic cables are finding increased application in a variety of products, and in particular, in aircraft design. Because of this increased use, instruments for measuring attenuation in such cables are becoming more prevalent. One method of conducting attentuation measuring systems for measuring the attenuation in such fiber optic cables is disclosed in U.S. Pat. No. 4,234,253, issued Nov. 18, 1980, and assigned to the assignee of the present invention. The drawings and specification disclosed in the U.S. Pat. No. 4,234,253 are incorporated herein by reference. In the U.S. Pat. No. 4,234,253, a timing pulse is generated in the receiver and combined with a test signal for transmission. These signals thereafter are separated in the receiver and the timing pulse is used to demodulate the test signal to provide a DC level voltage proportional to the amplitude of the signal wave transmitted through the cable. The DC voltage thus developed was compared with a reference signal and the difference between the received DC voltage and the reference signal was displayed as attenuation.

The invention described hereinafter, while applicable to similar attenuation determining problems, differs from the invention described in the U.S. Pat. No. 4,234,253 in several important design respects. In the present invention, one of the receiver and transmitter is designed to provide what may be considered as a digital signal for processing in the receiver, the digital signal being based on a transmitted reference signal. That is to say, a simple RC network may be utilized to provide a time uniform train of pulses, the pulses decreasing in amplitude by equal decibel values. This train of pulses may be generated at the transmitter and transmitted through a medium under test, or it may be generated in the receiver based on a signal received through the medium from a simplified transmitter. In the first instance, the pulse is used to count down a preset electronic counter. In the second case, the counter counts up. In both cases, the count in the counter after passage of the pulses is displayed as attenuation. When the pulse is generated in the receiver, the receiver, through suitable circuit switching arrangements, may be utilized as an optical power meter. Because of the simplicity of design, the invention provides an extremely low cost, simple and versatile device.

One of the objects of this invention is to provide a system for testing the transmission capabilities of fiber optical conductors.

Another object of this invention is to provide a test system for a medium employing a transmitter and receiver, which may be separate units interconnected only by the medium under test.

Another object of this invention is to provide a test device which functions both as an attenuation meter and a power meter.

Another object of this invention is to provide an attenuation meter for fiber optic cables which utilizes digital processing.

Other objects of this invention will be apparent to those skilled in the art in light of the following description and accompanying drawings.

SUMMARY OF THE INVENTION

In accordance with this invention, generally stated, a system for testing an electromagnetic wave transmitting medium is provided which includes a transmitter for transmitting a test signal through the medium. A receiver is positioned for reception of the test signal at a spaced location with respect to the transmitter. A circuit is provided for converting an analog signal generated in the transmitter to a pulsed signals for processing in the receiver. In the preferred embodiment, the conversion is accomplished in the transmitter. The receiver includes a counter which is counted down from a preset value by the pulsed signals received at the receiver. Any count remaining in the counter represents attenuation of the medium and is so displayed.

BRIEF DESCRIPTION OF THE DRAWINGS

In the drawings, FIG. 1 is a block diagrammatic view of a transmitter for one illustrative embodiment of system for measuring attenuation in an electromagnetic wave transmitting medium;

FIG. 2 is a representation of the electrical signals present at various positions in the transmitter of FIG. 1;

FIG. 3 is a block diagrammatic view of a receiver employed with the transmitter of FIG. 1;

FIG. 4 is a block diagrammatic view of of a transmitter for a second illustrative embodiment of a system for measuring attenuation in an electromagnetic wave transmitting medium;

FIG. 5 is a block diagrammatic view of a receiver employed with the transmitter of FIG. 4;

FIG. 7 is a block diagrammatic view of a circuit arrangement adaption of the transmitter shown in FIG. 4; and FIG. 8 is a representation of the electrical signal present at various times in the operation of the circuit of FIG. 7.

DESCRIPTION OF THE PREFERRED EMBODIMENT

Figure 6:
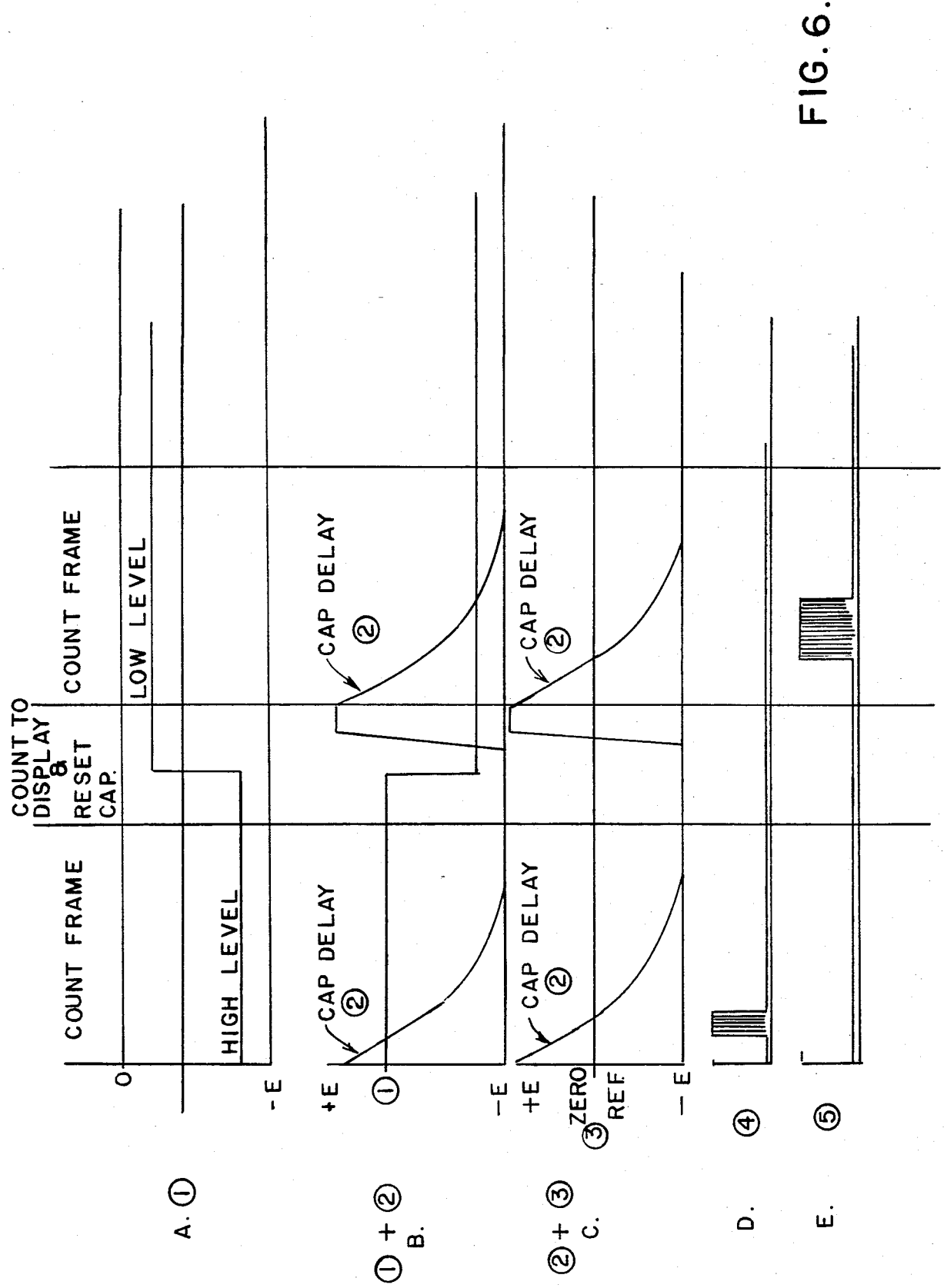
FIG. 6 is a representation of the electrical signals present at various positions in the receiver of FIG. 5.

Referring now to FIG. 1, reference numeral 1 indicates one illustrative embodiment of transmitter of this invention. The transmitter 1 includes a suitable timing device or clock 2 which is used to coordinate the functions of the transmitter 1. The clock is operatively connected to a counter 3. Counter 3 in turn is operatively connected to a pulse generator 4 along a conductor 5 and to a log amplitude generator 6 along a conductor 7. An output 8 of the log amplitude generator 6 forms an input to a sample and hold circuit means 9. The sample and hold circuit 9 has an output 10 connected to a gate electrode of a field effect transistor switch 11. The sample and hold means 9 is operatively connected to the pulse generator 4 along an output 12.

An output 13 of the pulse generator 4 is operatively connected to the source electrode of the field effect transistor switch 11. The drain electrode of the field effect transistor switch 11 is connected via a conductor 15 to a first input of a differential amplifier 16. An output 17 of the differential amplifier 16 forms an input to a drive amplifier 18.

The drive amplifier 18 powers a light emitting diode 19 which generates electromagnetic wave energy through a beam splitter 20. The beam splitter 20 permits passage of the electromagnetic wave energy through a particular medium. In the embodiment illustrated, the medium under test is a fiber optic cable, indicated generally by the reference numeral 25. Those skilled in the art will recognize that other mediums may be tested with the device disclosed herein. The beam splitter 20 directs a portion of the output of the diode 19 toward a photodetector 21. The output of the photodetector 21 is an input to an amplifier 22 which provides an output voltage proportional to the current signal of the photodetector 21. An output 23 of the amplifier 22 forms a second input to the differential amplifier 16. The feedback from the output side of the light emitting diode 19 provided at the output 23 of the amplifier 22 provides compensation for anomalies occurring in the operation of the light emitting diode 20 caused by temperature variations or variations in the drive amplifier 18, for example.

The generation of an analog log curve is accomplished by charging a precision capacitor preferably with low leakage and good stability, to a precise regulated voltage. The capacitor then is discharged through a precision resistor. This is accomplished in the log amplitude generator 6. At the same instant, the clock 2 is gated to start generating uniformly time spaced pulses in the pulse generator 4. The pulses gate the sample and hold circuit 9, which samples the decaying voltage at the output 8 of the log amplitude generator 6, once for each pulse. The pulse output of the pulse generator 4 also controls the field effect transistor 11 to gate the stepped levels in the sample and hold circuit 9 to the differential amplifier 16. Since the decibel to time relationship is linear, each pulse is precisely decreased by the same number of decibels. The electrical pulses are converted to electromagnetic wave energy at the diode 19, and transmitted through the cable 25.

FIG. 2 represents various wave forms present in the transistor 1 of FIG. 1. It may be observed that the capacitor of the log amplitude generator 6 is charged to a voltage V, and then allowed to discharge through a precision resistor for a time period K. The signal at the output 8 is shown in FIG. 2A. The output of the pulse generator 4 is shown in FIG. 2B. Finally, the signal at the output 15 of the field effect transistor 11 is shown in FIG. 2C.

As indicated, the remaining circuitry comprises a drive and linearizing network to convert the voltage pulses at the output 15 to pulses of light power following the same amplitude relationship. This is accomplished by the amplifier 18 for the light emitting diode 19, which drives the light emitting diode 19 to full capability, or any desired output level. The light delivered to the fiber optic cable 25 or other medium, is sampled by the photodetector 22 whose linearity is a major factor in accuracy. The amplified output of the photodetector 21 is applied in a degenerative feedback manner to the differential amplifier so that the output light is precisely matched to the voltage input of the differential amplifier 16. The accuracy of the match is a function of the loop gain, amplifier stability, and drift terms.

A receiver 30 compatible with the transmitter 1 is illustrated in FIG. 3. As there shown, the light from the light emitting diode 19, after passing through the fiber optic cable 25 or other medium, impinges a photodetector 31. The signal output of the detector 31 is an input at 32 to a transfer impedence amplifier 37. The input signal passes through three stages of amplification in the embodiment illustrated. That is to say, the signal is amplified by the amplifier 37, by a second stage amplifier 38, and by a final amplifier stage and limiter 39.

An output 40 of the amplifier and limiter 39 forms an input to a sample and hold circuit and amplifier means 41. The sample and hold means 41 has an output 42 forming an input to a low pass filter 43 and an output 44 operatively connected to an output side 45 of a data gap detector 46, the purpose and function of which are more fully discussed hereinafter.

An output 47 of the low pass filter 43 forms a first input to a summing means 48. A second input to the summing means 48 is obtained from an output 49 of an adjustment means 50, also discussed hereinafter.

An output 51 of the summing means 48 is an input to a comparator 52. The output 40 of the amplifier and limiter means 39 forms a second input to the comparator 52.

An output 53 of the comparator 52 is an input to a pulse duration filter 54. An output 55 of the filter 54 is an input to the gap detector 46 at 56 and to a strobe and preset means 57 along an input 58. The output 45 of the gap detector 46 is an input to a scaling counter 59. An output 60 of the scaling counter 59 is a second input to the strobe and preset means 57. An output 61 of the strobe and preset means 57 is an input to a presetable up/down counter 62. An output 63 of the counter 62 is an input to a latch and display driver means 64. The display driver means 64 in turn has an output side 65 operatively connected to a suitable display device 66.

Operation of the receiver 30 is relatively simple to understand. The decreasing level pulses from the transmitter 1 are coupled to the receiver photodiode 31 by the medium to be tested, in this case the fiber optic cable 25. As indicated, other electromagnetic wave transmittable mediums may be employed, if desired. The output of the receiving photodetector 31 is amplifier limited to prevent saturation in the stages 38 and 39. The detector amplifier system represented by the stages 37, 38 and 39 need not be linear over a large range as it need only reliable detect the smallest pulse of the total number of pulses in the measurement range provided, and not saturate and miss larger pulses. The sample and hold network 41 is operated when no pulses are present and removes the error that might be caused by diode detector 31 leakage or amplifier offsets. In addition, the adjustment reference 50 may be utilized to set the level of comparator 52. When a pulse exceeds this level, the comparator 52 is triggered to provide an output pulse at 53 and deliver it to a duration filter 54. The filter 54 normalizes the pulse length and amplitude. That pulse information is fed to the strobe and preset means 57 which in turn strobes the counter 62.

Gaps in the pulses or frames are detected by the gap detector means 46. During the data gap between pulse groups or frames, the counter 62 is preset to a number representing the total predecided decibel range. The presetting is accomplished through the scaling counter 59. The detected pulses on the output 55 count the counter 62 down from this preset number. If all of the pulses pass through the medium under test, the counter 62 will end at zero, indicating no loss. Attenuation in the coupling medium results in loss of lower pulses, thereby resulting in a count remaining in the counter 62, that count being utilized for the precise attenuation readout at the display 66.

The scaling counter 59 is necessary for matching the counter display with the reading that represents the amplitude difference between pulses and to provide sum averaging to minimize error from random pulses. Each frame may be counted many times to give an average reading.

It will be observed, by those skilled in the art, the only components requiring great stability in the receiver are the adjustable reference 50 used to set the minimum detectable pulse amplitude and the comparator that detects the pulse. All other components may be commercial grade integrated circuits and components.

As indicated above, generation of the log signal may be accomplished in either the transmitter or the receiver. The embodiment of the invention shown in FIGS. 4 and 5 accomplishes the analog signal generation in the receiver. Because of generation in the receiver, a transmitter 100 is substantially simplified from that shown in FIG. 1. As shown in FIG. 4, a voltage generator 101 forms an input to a preamplifier 102 having an output side 103. The output 103 is an input to a mixer amplifier 104. An output 105 of the amplifier 104 is an input to a light emitting diode driver amplifier 106. An output 107 of the driver amplifier 106 drives a light emitting diode 108 which transmits electromagnetic wave energy through a suitable medium, which again may comprise the fiber optic cable 25, if desired. A portion of the output again is sampled by a photodetector 109, and amplified in an amplifier 110. An output 111 of the amplifier 110 forms an input to the amplifier 104 for the same purpose as previously described.

Referring now to FIG. 5, a receiver 30a is shown in greater detail. The output of the light emitting diode 108 is an input to a photodetector 120. The signal detected by the photodetector 120 is amplified by a transimpedence amplifier 121. The amplifier 121 has an output 122 which is fed, through a resistor 123, to a comparator 124. The comparator 124 also has a second voltage impressed at its input side, developed across a resistor 125. The resistor 125 is connected to an output side 126 of an operational amplifier 127. An input 128 of the operational amplifier 127 is connected to a capacitor resistive circuit including a capacitor 129 and a resistor 130, connected in parallel between the input side of the operational amplifier 127 and ground.

A frame oscillator 130 has an output 131 connected to the gate electrode of an analog switch 132. The switch 132 operates to charge the capacitor 129 through a resistor 133 when activated by the frame oscillator 130, as later described in greater detail. The switch 132 connects a biased power supply 134 to the capacitor 129. The power supply 134 also is connected to an input 135 of a comparator 136 through a resistor 137 and a resistor 139. A zero reference adjustment resistor 140 is connected between ground and the connector of the resistor 139 and 137.

An output side 150 of the comparator 124 is connected directly to a NOR gate 181. The output 150 also is connected to a NOR gate 151 through an inverting amplifier 152. An output 153 of the comparator 136 is connected to the NOR gate 151 at an input 154 thereof and to the NOR gate 181 along an input 155 thereof and an inverting amplifier 156.

The oscillator 130 also is connected to the NOR gates 150 and 151 along an output 160. A scaling oscillator 161 has an output 162 also connected to the NOR gates 181 and 151, respectively. An output 163 of NOR gate 150 is connected to an OR gate 166 and to a flip/flop 167. An output 168 of NOR gate 151 is connected to the OR 166 and to the flip/flop 167. An output 168 of the OR gate 166 is connected to a counter display driver means 170. An output 171 of the flip/flop 167 also is connected to the counter display driver means 170.

The light received at the photodetector 120 is amplified by the transimpedence amplifier 121. In this embodiment of our invention, the light input to the photodetector 20 is assumed to be a steady state level. Those skilled in the art will appreciate, however, that with the use of the modulators or peak detectors, or other conditioning devices, modulated light could be detected as long as the light level is translated into a direct current voltage at 1 in FIG. 5. The voltage at 1 is illustrated in FIG. 6 at 6A. Two different levels are shown in that Figure to illustrate the measuring technique.

At the beginning of a measurement frame, the capacitor 129 is charged to a voltage higher than any expected from the amplifier 121. Charging of capacitor 129 is accomplished by activation of the switch 132, which connects the bias supply 134 at the proper designated time coincident with the beginning of a measurement interval or frame. In each measurement frame, the capacitor 129 will first be charged, and then allowed to discharge through resistor 131 upon the reopening of the switch 132. As will be appreciated by those skilled in the art, the discharge of the capacitor through resistor 131 is an exponential decay so that the elapsed time from the beginning of the voltage decay is proportional to the logarithm of the capacitor voltage. The capacitor voltage is used as a reference to measure the incoming voltage with reference to a second voltage.

The comparator 124 adds the decaying capacitor voltage at the output side 126 of the amplifier 127 to the transmitted light proportional voltage at the output side 122 of the amplifier 121 to give a result shown in FIG. 2B. The comparator output is positive when the voltage output at 126 exceeds the magnitude of the voltage output at 121 and is zero when the reverse is true. The comparator 136 functions in the same way in that it produces a positive voltage at its output side 153 when the capacitor voltage exceeds the reference voltage from the bias power supply 134 and the output at 153 is zero when it does not. The outputs 150 and 153 of the comparators 124 and 136, respectively, establish two truth conditions to open two different NOR gates, 181 and 151, respectively. The NOR gates 181 and 151 will be high only when all of their respective inputs are low. All inputs to NOR gate 181 are low when the capacitor voltage is lower than the voltage at the output side 122 of the amplifier 121 and higher than the reference voltage at 135 to the comparator 136. The inversion of logic on comparator 136 causes the inversion of the comparison between the voltage at 135 and 126. Also required for the NOR gate 181 to go high is that the frame oscillator be low in the measurement interval. The input from the oscillator 130 is necessary only to reduce the possibility of a spurious count during the reset operations, and the scale oscillator 161 to be low. During the time of the first three low conditions, the frame oscillator 130 will go high and low many times since its purpose is to time the interval of time that the capacitor voltage is between the value of the input voltage to the receiver 30a and that of the reference voltage provided by the biased power supply 134. The result is that a burst of pulses at the scale oscillator 160 frequency appears at the output 163 of the NOR gate 181 where they are gated to the counter 170 through OR gate 166. These counted pulses are transferred to the display 170 at the end of the frame and represent the time interval for the capacitor to decay between the two voltages. This time interval may be scaled and subdivided into any count so that it will digitally represent the measurement on a log scale. In the case of light, the units generally are in decibels which are equal to ten times the log to the base 10 of the output at 122 divided by the voltage at the input 135 to the comparator 136. The scale oscillator 161 may be adjusted to a frequency of one count per decibel, or at higher frequencies, for ten or hundred counts per decibel with the decimal point being positioned accordingly.

The second group of pulses shown in FIG. 6E are those present at the output side 168 of the NOR gate 151. They perform the same function as the pulses at the output 163 except that all of the logic is inverted so that the measurement is of a voltage below the reference. Consequently, the sign on the counter display is negative, the negative sign being occasioned by the resetting of the flip/flop 167 so that the sign bit is minus. The second count frame in FIG. 6E represents this measurement, that is to say, where the input voltage is lower than the reference voltage.

Those skilled in the art will appreciate that variations of the particular circuit arrangement are possible, and that other devices and scale measurements may be utilized, if desired. One particularly important variation changes the arrangement of capacitor 15, amplifier 127 and resistor 16 so that they form an integrator that is reset by the switch 132. That variation is shown in FIG. 7. As there shown, the switch 132 is connected to one side of resistor 131. The other side of resistor 131 is connected to the input side of amplifier 127. The resistor 133 is connected between an input voltage source on the input side of the amplifier 127. The capacitor 129 is connected between the output and input sides of the amplifier 127. The output side of the amplifier 127 is an input to the comparator 136. This rearrangement allows the capacitor 129 voltage to decrease linearly, as shown in FIG. 8. In this arrangement, the circuit produces a linear scale system useful in measuring linear functions such as temperature or voltage.

Numerous variations, within the scope of the appended claims, will be apparent to those skilled in the art in light of the foregoing description and accompanying drawings. For example, various minor changes may be made in the circuits disclosed, without departing from the scope intent of our invention. While a number of the circuits are shown and described in the block diagrammatic format as single lines, those skilled in the art will recognize that single line connections in block diagrammatic form often are multiple physical connections in actual embodiments of the invention. If additional information on the counter 170 is desired, it may be obtained in the *Intersil Data Book*, 1981 available from Intersil Inc., 10710 N. Tantair Avenue, Cupertino, Calif. 45015. These variations are merely illustrative.

Having thus described the invention, what is claimed and desired to be secured by Letters Patent is

1. A device for measuring attenuation, comprising:
    transmitter means for generating an electrical signal including means for converting said electrical signal to electromagnetic wave energy for transmission from said transmitting means;
    receiver means for receiving said electromagnetic wave energy from said transmitter means, including means for converting said electromagnetic wave energy to an electrical signal;
    means for converting said electrical signal to a plurality of pulses operatively connected to one of said transmitter means and said receiver means, said pulse converting means providing a plurality of pulses decreasing in amplitude by equal decibel values; and
    counter means presettable to a desired value operatively associated with said receiver means, said counter being counted down by said plurality of pulses, the count of said counter after count down corresponding to the attenuation of said electromagnetic wave energy during passage of said electromagnetic wave energy between said transmitter means and said receiver means.

2. The device of claim 1 wherein said electrical signal converting means includes a resistive and capacitive network.

3. The device of claim 2 wherein said converting means is operatively associated with said transmitter means.

4. The device of claim 3 wherein said converting means includes a log amplitude generator having said resistive and capacitive networks operatively associated with it, further including means for charging a capacitor of said capacitive network to a predetermined value, means operatively connected to said capacitor for causing the discharge of said capacitor through a resistor of said capacitive network, means for converting the voltage acrosss said resistor to a plurality of electrical pulses operatively connected to said resistor, and means for converting said electrical pulses to electromagnetic wave energy operatively connected to said converting means.

5. The device of claim 2 wherein said converting means is operatively associated with said receiver means.

6. The device of claim 5 wherein said wherein said converting means includes means for generating a transient voltage across a resistor of said resistive and capacitive network;
    means for comparing the transient voltage value across said resistor with said electrical signal operatively connected to said electrical signal means and said transient voltage generating means;
    means for generating a reference voltage;
    means for timing the decay of said transient voltage between the value of said electrical signal and said reference voltage operatively connected to said reference voltage generating means;
    means for generating a plurality of pulses based on the voltage decay between said reference voltage operatively connected to said comparing means;
    counter means operatively associated with said pulse generating means for counting said pulses; and
    means for displaying the count contained in said counter means after count down.

7. A device for measuring attenuation, comprising:
    transmitter means for generating electrical signals including means for converting said electrical signals to electromagnetic wave energy;
    receiver means for receiving said electromagnetic wave energy and for converting said electromagnetic wave energy into an electrical signal;

means associated with one of said transmitter means and receiver means for generating a plurality of pulses based on said generated electrical signal, said pulses decreasing in amplitude by equal decibel values;

counter means operatively connected to said receiver means and adapted to be counted down by said plurality of pulses; and means for displaying the count of said counter means at least after count down, operatively connected to said counter means.

8. The device of claim 7 wherein said means associated with one of said transmitter and said receiver means for generating a plurality of pulses based upon said generated electrical signal is operatively connected to said transmitter, further including a log amplitude generator containing a resistive and capacitive network, means for charging a capacitor of said resistive/capacitive network to a predetermined value, means for discharging said capacitor through said resistor operatively connected to said resistive and capacitive network, means for converting the voltage across said resistor to a plurality of electrical pulses operatively connected to said resistive and capacitive network, said converting means having an output side forming an input to said electromagnetic wave energy converting means.

9. The device of claim 8 wherein said receiver means further includes means for amplifying the electrical signal operatively connected to said means for converting said electric magnetic wave energy to an electrical signal, said counter means being presettable and operatively connected to said amplifier means.

10. The device of claim 7 wherein said means for generating a plurality of pulses is associated with said receiver means, further including:

means for generating a transient voltage across a resistor;

means for comparing the value of the transient voltage from said transient voltage generating means with the electrical signal at said receiver operatively connected to said electromagnetic wave energy converting means;

means for generating a reference voltage operatively connected to said receiver means;

means for timing the decay of the transient voltage of said transient voltage generating means between the value of said electrical signal and said reference voltage; and means for generating a plurality of pulses based on the voltage decay output between the value of said electrical signal and said reference voltage operatively connected to said timing means and said comparing means.

11. The device of claim 10 wherein said transmitter further includes a voltage generator, means for amplifying the voltage generated by said voltage generator operatively connected to said generator, photodiode means for converting said generated voltage to electromagnetic wave energy operatively connected to said amplifying means, and means for coupling a portion of the electromagnetic wave energy output of said photodiode means operatively connected between said photodiode and said amplifier means.

12. The device of claim 11 wherein said means for generating a transient voltage includes a capacitor and a resistor connected in parallel with one another to form an RC network, a power supply connected to said network, and a transistor switch operably connected between said power supply and said RC network.

13. A device for measuring attenuation, comprising:

a transmitter for generating electromagnetic wave energy including a log amplitude generator defined at least in part by a resistor and a capacitor arranged to define an RC network, means for converting the voltage across said resistor to a plurality of electrical pulses, said pulses decreasing in amplitude by equal decibel values, and means for converting said electrical pulses to electromagnetic wave energy operatively connected to said converting means; and a separate receiver for receiving said electromagnetic wave energy from said transmitter including means for converting the electromagnetic wave energy to an electrical signal, means for amplifying said electrical signal operatively connected to said converting means, a presettable counter operatively connected to said amplifier means so that said electrical signal counts said counter down from a preset value, and means for displaying the count remaining on said counter after countdown by said pulses.

* * * * *